(12) United States Patent
Smith et al.

(10) Patent No.: US 10,945,759 B2
(45) Date of Patent: Mar. 16, 2021

(54) MICRONEEDLE DEVICE

(71) Applicant: REFINE USA, LLC, Jacksonville Beach, FL (US)

(72) Inventors: Brian Smith, Jacksonville Beach, FL (US); Anthony A. Johnson, Tucson, AZ (US)

(73) Assignee: Refine USA, LLC, Jacksonville Beach, FL (US)

( * ) Notice: Subject to any disclaimer, the term of this patent is extended or adjusted under 35 U.S.C. 154(b) by 617 days.

(21) Appl. No.: 15/857,491

(22) Filed: Dec. 28, 2017

(65) Prior Publication Data

US 2019/0201673 A1 Jul. 4, 2019

(51) Int. Cl.
*A61B 17/16* (2006.01)
*A61B 90/00* (2016.01)
*A61B 17/34* (2006.01)
*A61B 17/00* (2006.01)
*A61M 37/00* (2006.01)

(52) U.S. Cl.
CPC .... *A61B 17/34* (2013.01); *A61B 2017/00367* (2013.01); *A61B 2017/00761* (2013.01); *A61M 2037/0023* (2013.01); *A61M 2037/0061* (2013.01)

(58) Field of Classification Search
CPC ..... A61M 37/0015–2037/0061; A61B 17/205; A61B 17/34; A61B 2017/00367; A61B 17/00761; A61B 5/1411; A61B 5/15142; A61B 5/15186; A61B 5/15146; A61B 5/15188
See application file for complete search history.

(56) References Cited

U.S. PATENT DOCUMENTS

| 2,542,828 A * | 2/1951 | Morrison ............ A61B 17/205 606/85 |
| 8,690,838 B2 | 4/2014 | Ozawa |
| 9,498,611 B2 | 11/2016 | Tokumoto |
| 2015/0112269 A1 | 4/2015 | Sumida |
| 2015/0133866 A1 | 5/2015 | Sumida |
| 2017/0173317 A1 | 6/2017 | Groop |

* cited by examiner

*Primary Examiner* — Tuan V Nguyen
(74) *Attorney, Agent, or Firm* — Mark Young. P.A, (57) ABSTRACT

A microneedle device includes an elastic sleeve to provide a biasing force and also to provide a fluid impermeable seal. The biasing force urges a barrel from the extended position to the retracted position. As a seal, the sleeve prevents contamination by fluids that may enter the barrel. Additionally, the distal end of the barrel features an undulating (waveform-like) formation to prevent suction buildup between the barrel and a patient's skin.

18 Claims, 8 Drawing Sheets

MICRONEEDLE DEVICE

FIELD OF THE INVENTION

This invention relates generally to a microneedle device, and, more particularly, to a microneedle assembly with an internal elastomeric seal and pressure relieving barrel.

BACKGROUND

Microneedle devices have been devised to treat, among other conditions, scars, acne scars, lines, wrinkles, stretch marks, melasma, and to improve skin texture and tighten the skin. Such devices are comprised of a plunger that reciprocates within a barrel. A plurality of fine needles (microneedles) protrude from the free end of the plunger and extend outwardly from the open end of the barrel when the plunger has reached its limit of travel towards the open end of the barrel. The microneedles create tiny punctures in the top layer of the skin, which triggers the body's healing process. By breaking up tethering in superficial scars and/or by breaking up melanocytes (cells in the epidermal layer of skin that produce a pigment called melanin), such devices give the treated area a chance to heal with less discoloration and/or deformation and greater smoothness on the surface.

A problem with existing microneedling devices is suction. The plunger fits tightly within the barrel. During rapid reciprocating motion, a seal formed between the skin and the open end of the barrel allows suction to develop. The suction interferes with proper performance of the device by drawing the treated area into the barrel.

A potential problem with existing microneedling devices is contamination of the hand tool that drives the microneedle assembly. The microneedle assembly is a replaceable cartridge. Such devices use a disposable needle cartridge affixed to the end of a hand tool. The hand tool reciprocates a rod of the microneedle assembly. A shaft of the hand tool pushes against the rod during a reciprocating stroke. The rod is coupled to the plunger of the microneedle assembly. Known microneedle assemblies contain springs to return the plunger to its retracted state. During a procedure, a patient's blood could possibly contaminate the microneedle assembly. In conventional microneedling devices it may be possible for blood to travel through the microneedle assembly to the hand tool.

What is needed is an improved microneedle assembly that alleviates suction while providing a fluid tight seal within the microneedle assembly, and works with existing hand tools. The invention is directed to overcoming one or more of the problems and solving one or more of the needs as set forth above.

SUMMARY OF THE INVENTION

To solve one or more of the problems set forth above, in an exemplary implementation of the invention, a microneedle device includes an elastic sleeve having a proximal end and a distal end. The proximal end of the sleeve and the distal end of the sleeve are open. A central channel extends through the sleeve. The sleeve is stretchable from a relaxed length to a stretched length. At the stretched length the sleeve exerts a tensile force urging return of the sleeve to the relaxed length. The sleeve is impermeable and may be comprised of a medical grade rubber, a medical grade polydimethylsiloxane or a medical grade fluoropolymer elastomer.

An exemplary microneedle device according to principles of the invention also includes a rod (i.e., a push rod) having a proximal end, a medial portion, a distal end, a proximal portion extending from the medial portion of the rod to the proximal end of the rod. The distal portion of the rod extends from the medial portion to the distal end of the rod. The distal portion of the rod extends through the central channel of the sleeve. The rod is movable linearly in reciprocating fashion relative to the proximal end of the sleeve. The reciprocating motion of the rod is between a retracted position and an extended position. The medial portion of the rod may include an annular concentric stop.

An exemplary microneedle device according to principles of the invention also includes a barrel having a proximal end and a distal end. The proximal end and distal end of the barrel are open. A central channel extends through the barrel from the distal end of the barrel to the proximal end of the barrel. The barrel is rigid. The distal end of the barrel includes a plurality of ridges and concave formations, such as in an undulating (wavelike) formation.

An exemplary microneedle device according to principles of the invention also includes a plunger having a proximal end, a distal end, and a body between the distal end of the plunger and the proximal end of the plunger. The distal end of the plunger includes a substantially planar surface. The body of the plunger is sized and shaped to fit within the central channel of the barrel and allow reciprocating linear motion of the plunger in the barrel. The distal end of the rod is coupled to the proximal end of the plunger. Reciprocating motion of the rod causes equal reciprocating motion of the plunger. The distal end of the elastic sleeve is coupled to the end of the plunger.

An exemplary microneedle device according to principles of the invention also includes a plurality of needles attached to and extending from the distal end of the plunger. The needles are contained within the central channel of the barrel when the rod is in the retracted position. The needles extend beyond the distal end of the barrel when the rod is in the extended position.

An exemplary microneedle device according to principles of the invention also includes a rigid sleeve housing. The sleeve housing is a hollow elongated cylinder with a proximal end and a distal end. The proximal and distal ends of the hollow elongated cylinder are open. A central channel extends through the hollow elongated cylinder from the distal end to the proximal end. The hollow elongated cylinder contains at least a substantial portion of the sleeve including the proximal end of the sleeve. The proximal end of the sleeve is coupled to the proximal end of the sleeve housing.

An exemplary microneedle device according to principles of the invention also includes a flanged bushing having an annular flange and a rigid tube. The tube extends perpendicularly from the annular flange. The annular flange and the tube are concentric. The tube is pressed within the proximal end of the sleeve within the proximal end of the sleeve housing and thereby secures the proximal end of the sleeve at the proximal end of the sleeve housing. The flange abuts the proximal end of the sleeve housing. The distal portion of the rod extends through the flanged bushing.

The elastic sleeve of an exemplary microneedle device according to principles of the invention provides a biasing force to urge the plunger from the extended position to the retracted position. Unlike springs used in conventional microneedle devices, the elastic sleeve also provides a fluid impermeable seal. Fluids that may enter the barrel cannot pass the sleeve. Thus, a tool to which the exemplary microneedle device is attached is protected from contamination.

The distal end of the barrel of an exemplary microneedle device according to principles of the invention prevents suction buildup between the barrel and a patient's skin. Preventing suction reduces trauma to the skin and facilitates healing.

BRIEF DESCRIPTION OF THE DRAWINGS

The foregoing and other aspects, objects, features and advantages of the invention will become better understood with reference to the following description, appended claims, and accompanying drawings, where:

Those skilled in the art will appreciate that the figures are not intended to be drawn to any particular scale; nor are the figures intended to illustrate every embodiment of the invention. The invention is not limited to the exemplary embodiments depicted in the figures or the specific components, configurations, shapes, relative sizes, ornamental aspects or proportions as shown in the figures.

DETAILED DESCRIPTION

An microneedle device according to principles of the invention includes a plunger within a barrel, a seal housing connected to one end of the barrel, a rod (i.e., push rod) that extends through the seal housing to the barrel, a plurality of needles protruding from an end of the plunger, and a tubular resilient elastomeric seal that is couples an end of the seal housing to an end of the plunger. The free end of the barrel includes a plurality of ridges, cutouts or concave formations that prevent suction buildup. In one embodiment, the free end of the barrel features an undulations (i.e., a wavelike form). The tubular resilient elastomeric seal stretches when the rod is driven towards the barrel, and returns to an unstretched or relaxed state when the rod is allowed to return to its original retracted position. The tubular resilient elastomeric seal provides a fluid-tight seal between the rod and the plunger.

Figure 1:
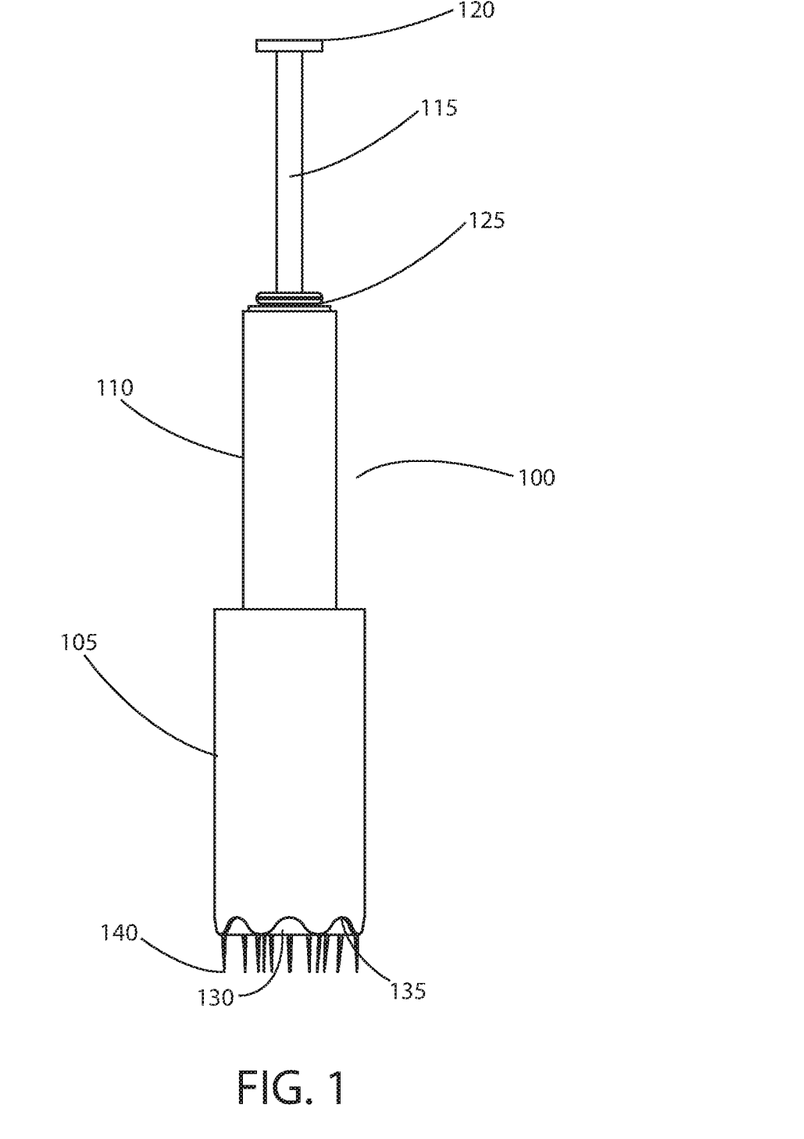
FIG. 1 is a front view of an exemplary microneedle device in a deployed state according to principles of the invention.
Figure 2:
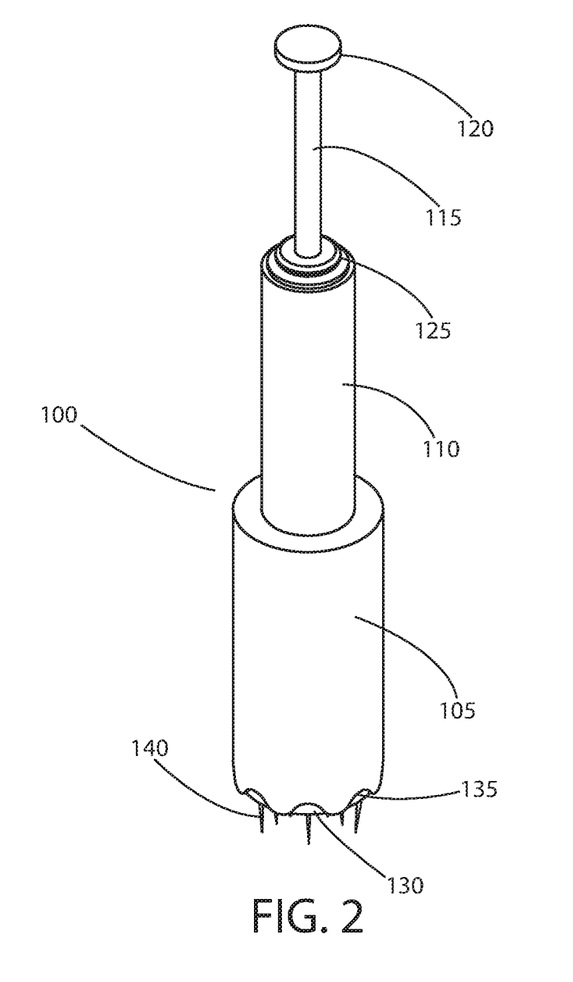
FIG. 2 is a front-top perspective view of an exemplary microneedle device in a deployed state according to principles of the invention.
Figure 3:
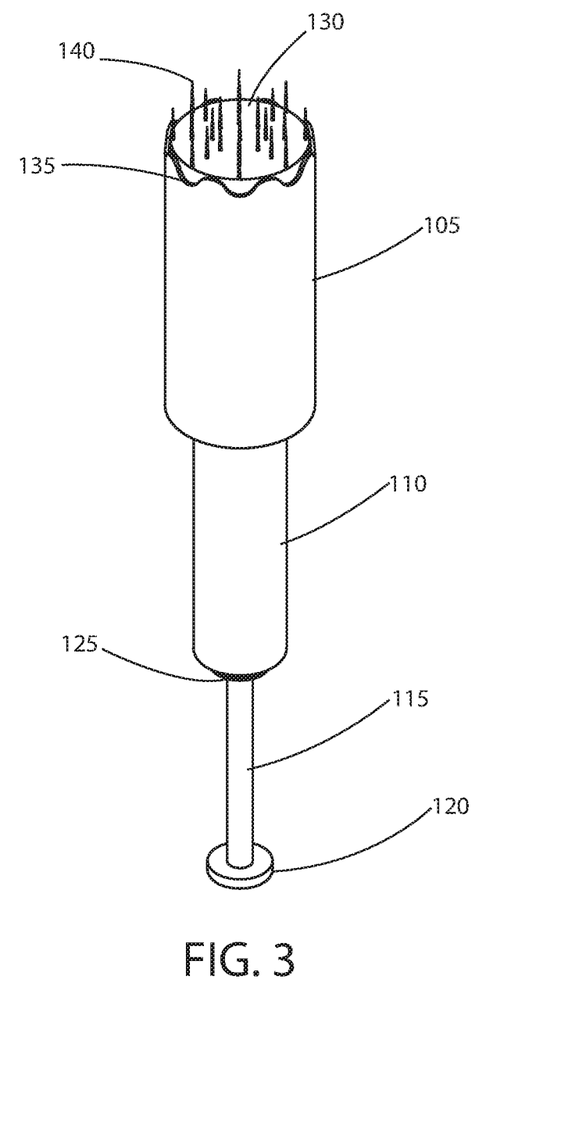
FIG. 3 is a front-bottom perspective view of an exemplary microneedle device in a deployed state according to principles of the invention.

Referring to FIGS. 1 through 3, an exemplary microneedle device 100 in an extended or deployed state is conceptually illustrated. In this state, a plurality of microneedles 140 extend from the plunger 130, beyond the end 135 of the barrel 105. This state is achieved by driving (i.e., pushing) the rod (i.e., push rod) 115 towards the barrel 105, by applying an adequate force to a flange 120 at the free end of the rod 115. An annular stop 125 attached to the rod 115 defines the maximum range of travel towards the barrel 105. When the stop 125 hits the end of the seal housing 110, the stop 125 impedes further travel of the rod towards the barrel 105. The rod 115 extends to and is attached to the plunger 130, which is contained in the barrel 105. Linear translation of the rod 115 causes linear translation of the plunger 130 within the barrel 105.

A resilient, elastomeric tubular seal (discussed below, aka elastic sleeve) is substantially contained in the seal housing 110 (sleeve housing), with one end attached to the end of the seal housing 110 away from the barrel 105 and the opposite end attached to the plunger 130. In the extended deployed state as shown in FIGS. 1 through 3, the resilient, elastomeric tubular seal is stretched.

In the extended deployed state as shown in FIGS. 1 through 3, the needles 140 protruding from the barrel 105 may be used for therapy. Typically, the needles are driven into and puncture the outer layers of skin, of an area to be treated. The area may include a scar, stretch marks or pigmentation to be alleviated upon healing.

The microneedle device attaches to a hand tool. The hand tool includes a reciprocating shaft. The shaft of the hand tool moves linearly from a retracted position to an extended position. Some tools include controls to adjust the frequency, i.e., the rate at which movement from a retracted position to an extended position occurs. The reciprocating shaft of the hand tool pushes against the flange 120 of the rod 115 during movement from the retracted position to the extended position. The amplitude (i.e., range of motion) of motion of the reciprocating shaft is about the same as that for the rod of the microneedle device. Thus, when the shaft of the tool has moved from a retracted position to an extended position, the rod 115 is moved from a retracted position to an extended position. Typical hand tools do not pull the rod 115 back from an extended position to the retracted position. Instead, a biasing means within the microneedle device urges the rod, plunger and needles from the extended position to the retracted position, as the shaft of the hand tool retracts. In the invention, the biasing means is a resilient elastomeric tubular sleeve, which also serves as a seal.

Figure 4:
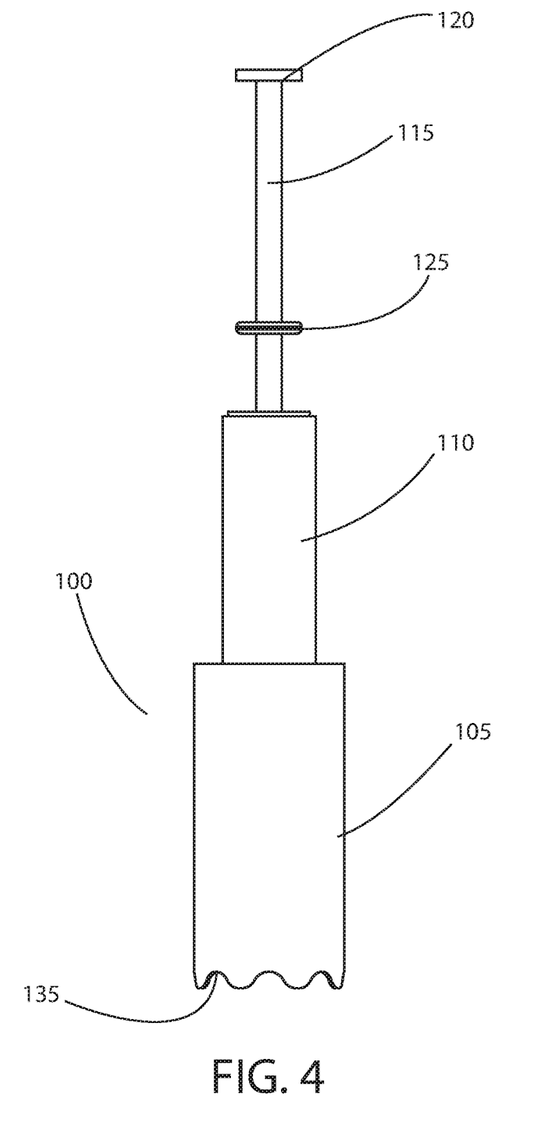
FIG. 4 is a front view of an exemplary microneedle device in a retracted state according to principles of the invention.
Figure 5:
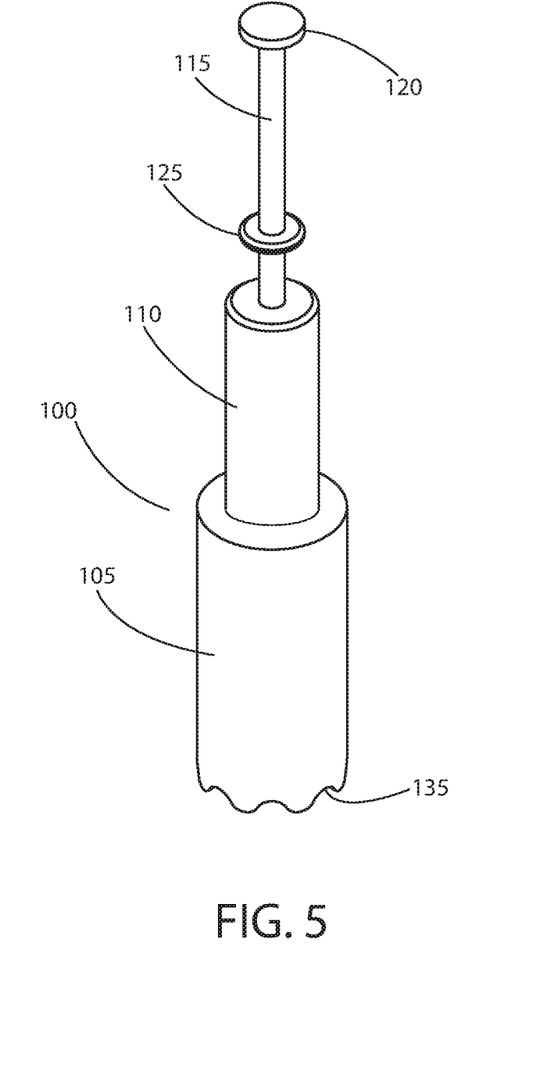
FIG. 5 is a front-top perspective view of an exemplary microneedle device in a retracted state according to principles of the invention.
Figure 6:
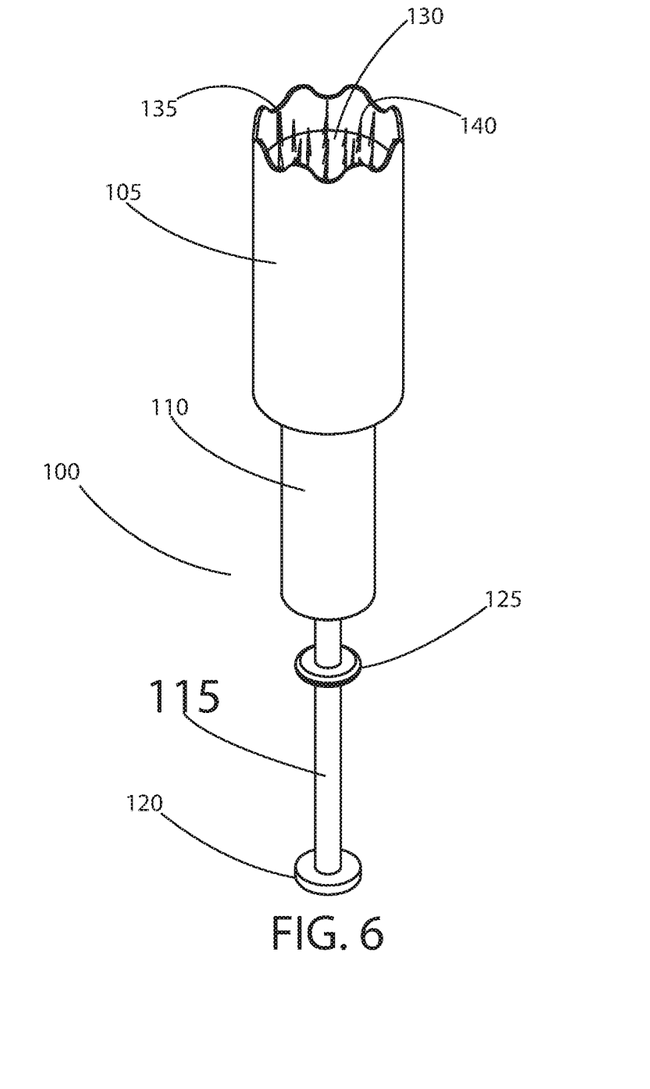
FIG. 6 is a front-bottom perspective view of an exemplary microneedle device in a retracted state according to principles of the invention.

FIGS. 4 through 6 conceptually illustrate the exemplary microneedle device 100 in a retracted state according to principles of the invention. In the retracted state, the plunger 130 and needles 140 have been withdrawn into the barrel 105. As the free end of the barrel 105 includes ridges, cutouts or concave formations, a seals does not form between the skin of a patient and barrel as the plunger 130 is withdrawn into the barrel 105. Thus, appreciable suction is avoided. Consequently, the skin is not sucked into the barrel during retraction. This is important because such suction interferes with operation of the microneedle device 100, bruises the area, and may delay healing and clotting.

In FIGS. 4 through 6, the rod 115 extends further from the seal housing 110. The stop 125, which is attached to the rod 115, has moved apart from the end of the seal housing 110. Within the seal housing 110 is the resilient elastomeric tubular sleeve in a less stretched or a substantially unstretched (i.e., relaxed) state.

Figure 7:
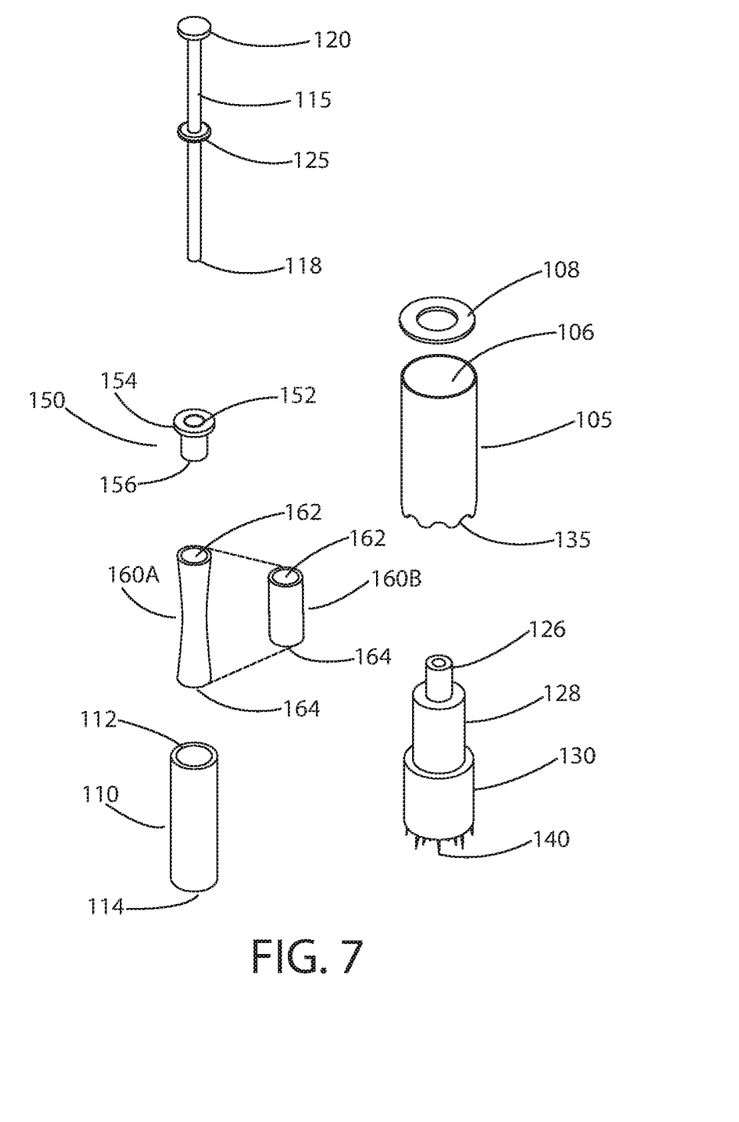
FIG. 7 is a front-top exploded perspective view of an exemplary microneedle device according to principles of the invention.
Figure 8:
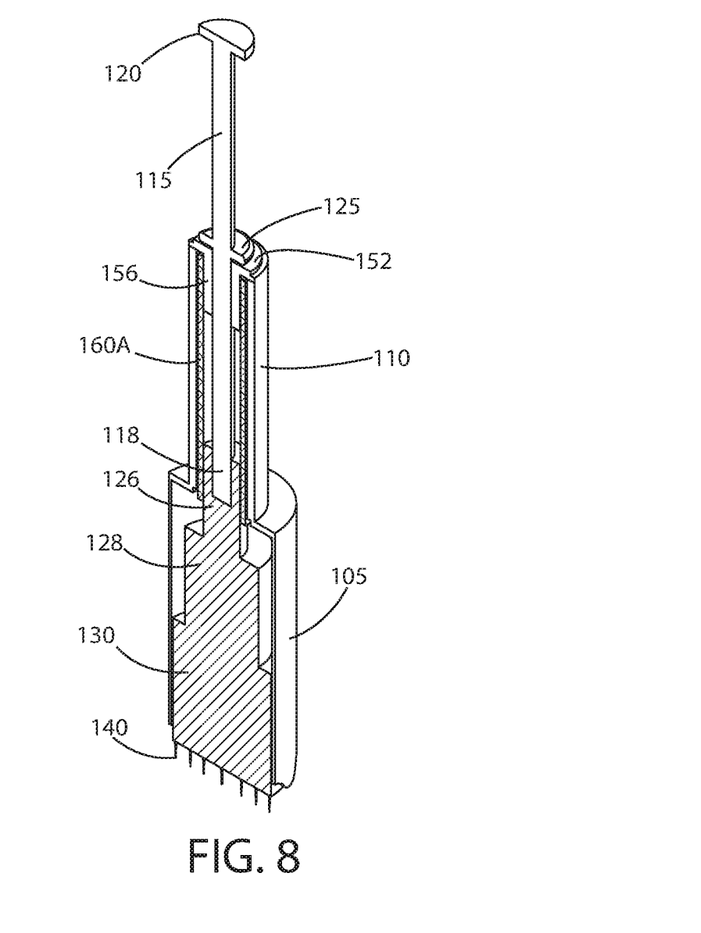
FIG. 8 is a front-top perspective view of a section of an exemplary microneedle device in a deployed state according to principles of the invention.

FIG. 7 provides a front-top exploded perspective view of an exemplary microneedle device according to principles of the invention. FIG. 8 provides a section view of an exemplary microneedle device according to principles of the invention. These views reveal several internal components that are not visible in FIGS. 1 through 6.

The rod 115 includes an end 118 that plugs into the sleeve bushing 126 extending from the neck 128 of plunger 130. The plunger 130 is a hollow or solid plastic cylinder with a closed end onto which the needles 140 are mounted. Other plunger configurations, such as syringe plunger configurations may be utilized without departing from the scope of the invention. The reduced diameter neck 128 of the exemplary plunger 130 is an optional feature. The plunger 130 may maintain a constant diameter to the sleeve bushing 126. In a syringe style plunger, a disc is formed or attached to the end of an elongated support structure having a +−shaped cross section.

The plunger 130 moves within the barrel 105 from a retracted to an extended position. Thus, the barrel 105 is long enough to house the plunger 130 and needles 140 in the retracted position, but not so long as to conceal the needles 140 in the extended position. Rather, in the extended position, the needles extend outward from and beyond the open end 135 of the barrel 105.

The barrel 105 includes an open end 135 with ridges and concave formations at the edge to prevent a seal at the skin. The barrel includes another end 106 with a cover 108 to which the seal housing 110 attaches. The cover 108 may be integrally formed with or attached to the end 106 of the barrel 105. The cover 180 is an annular structure (i.e., a disc with a central aperture). The central aperture has a diameter that is about the same as the inner diameter of the seal housing 110, and that is greater than the outer diameter of the sleeve bushing 126, and that is greater than the outer diameter of the resilient elastomeric tubular seal 160A, 160B.

The seal housing 110 is a plastic tube, with an end 114 that attaches to the end cover 108 of the barrel 105. The opposite end 112 receives an end 162 of the resilient elastomeric tubular seal 160A, and the sleeve 156 of the flanged bushing 150. The seal housing 110 is at least about as long as the resilient elastomeric tubular seal 160A in its stretched (i.e., extended) state. The inner diameter of the seal housing 110 is at least as large as the outer diameter of the resilient elastomeric tubular seal 160A.

A flanged bushing 150 retains an end 162 of the resilient elastomeric tubular seal 160A between the sleeve 156 of the bushing and the end 112 of the resilient elastomeric tubular seal 160A. The retained end 162 of the resilient elastomeric tubular seal 160A is securely clamped between the sleeve 156 of the bushing 150 and the inner surface of the end 112 of the seal housing 110. The sleeve 156 of the bushing 150 with the retained end 162 of the resilient elastomeric tubular seal 160A are tightly fitted in the end 112 of the seal housing 110. To further prevent separation of the end 162 of the resilient elastomeric tubular seal 160A from the sleeve 156 of the flanged bushing 150, the end 162 of the resilient elastomeric tubular seal 160A may be frictionally retained, clamped, welded or bonded to the sleeve 156.

The flange 154 of the flanged bushing 150 has an outer diameter that is larger than the inner diameter of the seal housing 110, and preferably about the same as the outer diameter of the seal housing 110. The flanged bushing also includes a central channel 152 having a diameter that is slightly larger than the diameter of the rod 115. Thus, the portion of the rod 115 from the end 118 to the stop 125 may slide through the channel 152.

The resilient elastomeric tubular seal is shown in a stretched (i.e., extended) configuration 160A and in an unstretched (i.e., relaxed) configuration. One end 162 of the seal attaches to the sleeve 156 of the flanged bushing 150 at the end 112 of the seal housing 110. The other end 164 of the seal attaches to the sleeve bushing 126 at the end of the neck 128 of the plunger 130. The end 164 of the resilient elastomeric tubular seal may be frictionally retained, clamped, welded or bonded to the sleeve bushing 126.

The plunger assembly includes a plunger body (i.e., the plunger) 130, a neck 128 and a sleeve bushing 126. The rod 115 includes an end 118 that plugs into the sleeve bushing 126 extending from the neck 128 of plunger 130. The plunger assembly moves linearly within the barrel 105 from a retracted to and extended position. In the retracted position, the microneedles 140 are contained in the barrel 105. In the extended position, the microneedles 140 extend from the end 135 of the barrel 105. The plunger assembly may be solid or hollow (e.g., comprised of two hollow halves bonded together). The plunger assembly may, alternatively, be configured as a syringe style plunger, with a disc is formed or attached to one end of an elongated support structure having a +−shaped cross section, and a sleeve bushing attached to the other end. Such attachments may be by bonding, welding or integral molding.

A microneedle device 100 according to principles of the invention may be produced using any suitable manufacturing techniques known in the art for the chosen materials. Preferably the manufacturing technique is suitable for mass production at relatively low cost per unit, and results in an aesthetically acceptable product with a consistent acceptable quality and structural and functional characteristics. A microneedle device 100 according to principles of the invention may be assembled from pre-formed parts. The rod 115, flanged bushing 150, seal 160A, seal housing 110, barrel 105 with end cap 108, and plunger assembly 130 may each be produced as a separate component. The seal housing 110 may be attached to the cap 108 at the end 106 of the barrel 105, or integrally formed with the barrel 105. Most of the parts may be formed from injection molded thermoplastics such as polystyrene, polyethylene, polypropylene, polytetrafluoroethylene, and polyvinylchloride. A lubricant, such as medical grade silicone lubricant may be applied to the end 118 of the rod 115, the central channel 152 of the flanged bushing 150, the plunger assembly 130, and the interior of the barrel 105 for reducing friction. The needles 140 are preferably made of medical grade stainless steel and attached to the plunger by mechanical connection, welding, and/or adhesives such as heat curable and ultraviolet curable epoxy adhesives. The resilient elastomeric seal 160A is comprised of a medical grade rubber, polydimethylsiloxane (e.g., silicone) or fluoropolymer elastomer. It is desirable that the device 100 be sterile when used. Accordingly, all components used in the device be chosen and/or formulated to withstand a sterilization process being utilized.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A microneedle device comprising:
   a sleeve having a proximal end and a distal end, the proximal end of the sleeve being open, the distal end of the sleeve being open, a central channel extending through the sleeve from the proximal end of the sleeve to the distal end of the sleeve, the sleeve being elastic and stretchable from a relaxed length to a stretched length, and at the stretched length the sleeve exerting a tensile force, the tensile force urging return of the sleeve to the relaxed length, and the sleeve providing a fluid tight seal between the rod and the plunger; and
   a rod having a proximal end, a medial portion, a distal end, a proximal portion extending from the medial portion of the rod to the proximal end of the rod, and a distal portion extending from the medial portion to the distal end of the rod; the distal portion of the rod extending through the central channel of the sleeve, and the rod being movable linearly in reciprocating fashion relative to the proximal end of the sleeve, reciprocating motion of the rod being between a retracted position and an extended position; and
   a barrel having a proximal end and a distal end, the proximal end of the barrel being open, the distal end of the barrel being open, and a central channel extending through the barrel from the distal end of the barrel to the proximal end of the barrel, and the barrel being rigid; and
   a plunger having a proximal end, a distal end, and a body between the distal end of the plunger and the proximal end of the plunger, the distal end of the plunger including a substantially planar surface, the body of the plunger being sized and shaped to fit within the central channel of the barrel and allow reciprocating linear motion of the plunger in the barrel, and the distal end of the rod being coupled to the proximal end of the plunger, and reciprocating motion of the rod being between the retracted position and the extended position causing equal reciprocating motion of the plunger, and the distal end of the elastic sleeve being coupled to the proximal end of the plunger; and
   a plurality of needles attached to and extending from the distal end of the plunger, the plurality of needles being contained within the central channel of the barrel when the rod is in the retracted position, and the plurality of needles extending beyond the distal end of the barrel when the rod is in the extended position.

2. The microneedle device according to claim 1, the sleeve being impermeable.

3. The microneedle device according to claim 1, the sleeve being comprised of a material from the group consisting of a medical grade rubber, a medical grade polydimethylsiloxane and a medical grade fluoropolymer elastomer.

4. The microneedle device according to claim 1, the medial portion of the rod including an annular stop, the annular stop and rod being concentric.

5. The microneedle device according to claim 1, further comprising a sleeve housing, the sleeve housing comprising a hollow elongated cylinder with a proximal end and a distal end, the proximal end of the hollow elongated cylinder being open, the distal end of the hollow elongated cylinder being open, and a central channel extending through the hollow elongated cylinder from the distal end of the hollow elongated cylinder to the proximal end of the hollow elongated cylinder, and the hollow elongated cylinder being rigid, and the hollow elongated cylinder containing at least a substantial portion of the sleeve including the proximal end of the sleeve, and the proximal end of the sleeve being coupled to the proximal end of the sleeve housing.

6. The microneedle device according to claim 5, further comprising a flanged bushing including an annular flange and a tube, the tube extending perpendicularly from the annular flange, the annular flange and the tube being concentric, and the tube being pressed within the proximal end of the sleeve within the proximal end of the sleeve housing and thereby securing the proximal end of the sleeve at the proximal end of the sleeve housing, and the flange abutting the proximal end of the sleeve housing, and the distal portion of the rod extending through the flanged bushing.

7. The microneedle device according to claim 1, the distal end of the barrel including a plurality of concave formations.

8. The microneedle device according to claim 1, the distal end of the barrel including undulating formations.

9. The microneedle device according to claim 1,
   the sleeve being impermeable and comprised of a material from the group consisting of a medical grade rubber, a medical grade polydimethylsiloxane and a medical grade fluoropolymer elastomer; and
   the medial portion of the rod including an annular stop, the annular stop and rod being concentric; and
   the distal end of the barrel including undulating formations; and
   the microneedle device further comprising
   a sleeve housing, the sleeve housing comprising a hollow elongated cylinder with a proximal end and a distal end, the proximal end of the hollow elongated cylinder being open, the distal end of the hollow elongated cylinder being open, and a central channel extending through the hollow elongated cylinder from the distal end of the hollow elongated cylinder to the proximal end of the hollow elongated cylinder, and the hollow elongated cylinder being rigid, and the hollow elongated cylinder containing at least a substantial portion of the sleeve including the proximal end of the sleeve, and the proximal end of the sleeve being coupled to the proximal end of the sleeve housing; and a flanged bushing including an annular flange and a tube, the tube extending perpendicularly from the annular flange, the annular flange and the tube being concentric, and the tube being pressed within the proximal end of the sleeve within the proximal end of the sleeve housing and thereby securing the proximal end of the sleeve at the proximal end of the sleeve housing, and the flange abutting the proximal end of the sleeve housing, and the distal portion of the rod extending through the flanged bushing.

10. A microneedle device comprising:
    a barrel having a proximal end and a distal end, the proximal end of the barrel being open, the distal end of the barrel being open, and a central channel extending through the barrel from the distal end of the barrel to the proximal end of the barrel, and the distal end of the barrel including a plurality of concave formations, and the barrel being rigid; and a plunger having a proximal end, a distal end, and a body between the distal end of the plunger and the proximal end of the plunger, the distal end of the plunger including a substantially planar surface, the body of the plunger being sized and shaped to fit within the central channel of the barrel and allow reciprocating linear motion of the plunger in the barrel; and a rod having a proximal end, a medical portion, a distal end, a proximal portion extending from the medial portion of the rod to the proximal end of the rod, and a distal portion extending from the medial portion to the distal end of the rod; the rod being movable linearly in reciprocating fashion relative to the proximal end of the barrel, reciprocating motion of the rod being between a retracted position and an extended position, and the distal end of the rod being coupled to the proximal end of the plunger, and reciprocating motion of the rod being between the retracted position and the extended position causing equal reciprocating motion of the plunger; and a biasing means coupled to the plunger, the biasing means urging the plunger, and the rod coupled to the proximal end of the plunger, towards the retracted position; and a plurality of needles attached to and extending from the distal end of the plunger, the plurality of needles being contained within the central channel of the barrel when the rod is in the retracted position, and the plurality of needles extending beyond the distal end of the barrel when the rod in the extended position; and the biasing means comprising a sleeve having a proximal end and a distal end, the proximal end of the sleeve being open, the distal end of the sleeve being open, a central channel extending through the sleeve from the proximal end of the sleeve to the distal end of the sleeve, the sleeve being elastic and stretchable from a relaxed length to a stretched length, and at the stretched length the sleeve exerting a tensile force, the tensile force urging return of the sleeve to the relaxed length, and the sleeve providing a fluid tight seal between the rod and the plunger.

11. The microneedle device according to claim 10, the sleeve being impermeable.

12. The microneedle device according to claim 10, the sleeve being comprised of a material from the group consisting of a medical grade rubber, a medical grade polydimethylsiloxane and a medical grade fluoropolymer elastomer.

13. The microneedle device according to claim 10, further comprising a sleeve housing, the sleeve housing comprising a hollow elongated cylinder with a proximal end and a distal end, the proximal end of the hollow elongated cylinder being open, the distal end of the hollow elongated cylinder being open, and a central channel extending through the hollow elongated cylinder from the distal end of the hollow elongated cylinder to the proximal end of the hollow elongated cylinder, and the hollow elongated cylinder being rigid, and the hollow elongated cylinder containing at least a substantial portion of the sleeve including the proximal end of the sleeve, and the proximal end of the sleeve being coupled to the proximal end of the sleeve housing.

14. The microneedle device according to claim 13, further comprising a flanged bushing including an annular flange and a tube, the tube extending perpendicularly from the annular flange, the annular flange and the tube being concentric, and the tube being pressed within the proximal end of the sleeve within the proximal end of the sleeve housing and thereby securing the proximal end of the sleeve at the proximal end of the sleeve housing, and the flange abutting the proximal end of the sleeve housing, and the distal portion of the rod extending through the fanged bushing.

15. The microneedle device according to claim 10, the concave formations at the distal end of the barrel being part of an undulating formation.

16. A microneedle device comprising:

a sleeve having a proximal end and a distal end, the proximal end of the sleeve being open, the distal end of the sleeve being open, a central channel extending through the sleeve from the proximal end of the sleeve to the distal end of the sleeve, the sleeve being elastic and stretchable from a relaxed length to a stretched length, and at the stretched length the sleeve exerting a tensile force, the tensile force urging return of the sleeve to the relaxed length, and the sleeve providing a fluid tight seal between the rod and the plunger; and a reciprocating rod having a proximal end, a medial portion, a distal end, a proximal portion extending from the medial portion of the reciprocating rod to the proximal end of the reciprocating rod, and a distal portion extending from the medial portion to the distal end of the reciprocating rod; the distal portion of the reciprocating rod extending through the central channel of the sleeve, and the reciprocating rod undergoing reciprocating motion relative to the proximal end of the sleeve, the reciprocating motion of the reciprocating rod being between a retracted position and an extended position; and a barrel having a proximal end and a distal end, the proximal end of the barrel being open, the distal end of the barrel being open, and a central channel extending through the barrel from the distal end of the barrel to the proximal end of the barrel, and the barrel being rigid; and a plunger having a proximal end, a distal end, and a body between the distal end of the plunger and the proximal end of the plunger, the distal end of the plunger including a substantially planar surface, the body of the plunger being sized and shaped to fit within the central channel of the barrel and allow reciprocating linear motion of the plunger in the barrel, and the distal end of the reciprocating rod being coupled to the proximal end of the plunger, and reciprocating motion of the reciprocating rod being between the retracted position and the extended position causing equal reciprocating motion of the plunger, and the distal end of the elastic sleeve being coupled to the proximal end of the plunger, and a plurality of needles attached to and extending from the distal end of the plunger, the plurality of needles being contained within the central channel of the barrel when the reciprocating rod is in the retracted position, and the plurality of needles extending beyond the distal end of the barrel when the reciprocating rod is in the extended position.

17. The microneedle device according to claim 16, further comprising a sleeve housing, the sleeve housing comprising a hollow elongated cylinder with a proximal end and a distal end, the proximal end of the hollow elongated cylinder being open, the distal end of the hollow elongated cylinder being open, and a central channel extending through the hollow elongated cylinder from the distal end of the hollow elongated cylinder to the proximal end of the hollow elongated cylinder, and the hollow elongated cylinder being rigid, and the hollow elongated cylinder containing at least a substantial portion of the sleeve including the proximal end of the sleeve, and the proximal end of the sleeve being coupled to the proximal end of the sleeve housing; and     a flanged bushing including an annular flange and a tube, the tube extending perpendicularly from the annular flange, the annular flange and the tube being concentric, and the tube being pressed within the proximal end of the sleeve within the proximal end of the sleeve housing and thereby securing the proximal end of the sleeve at the proximal end of the sleeve housing, and the flange abutting the proximal end of the sleeve housing, and the distal portion of the reciprocating rod extending through the flanged bushing.

18. The microneedle device according to claim 17, the distal end of the barrel including an undulating formation.

\* \* \* \* \*